(12) United States Patent
Jonsen et al.

(10) Patent No.: US 7,822,488 B2
(45) Date of Patent: Oct. 26, 2010

(54) SELF-STORING MEDICAL ELECTRODES

(75) Inventors: Eric Jonsen, Seattle, WA (US); Daniel Powers, Issaquah, WA (US); Gregory Brink, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 218 days.

(21) Appl. No.: 10/599,113

(22) PCT Filed: Mar. 16, 2005

(86) PCT No.: PCT/IB2005/050928

§ 371 (c)(1),
(2), (4) Date: Sep. 20, 2006

(87) PCT Pub. No.: WO2005/092430

PCT Pub. Date: Oct. 6, 2005

(65) Prior Publication Data

US 2007/0203558 A1    Aug. 30, 2007

Related U.S. Application Data

(60) Provisional application No. 60/556,132, filed on Mar. 23, 2004.

(51) Int. Cl.
*A61N 1/39* (2006.01)
(52) U.S. Cl. ........................ 607/142; 206/701
(58) Field of Classification Search ............... 600/392; 607/5, 142, 152; 206/701–728
See application file for complete search history.

(56) References Cited

U.S. PATENT DOCUMENTS 3,556,105 A * 1/1971 Shepard ................. 607/152
3,961,623 A 6/1976 Milani et al.
4,034,854 A * 7/1977 Bevilacqua ............... 206/370
4,419,998 A * 12/1983 Heath ..................... 600/391
4,750,482 A 6/1988 Sieverding et al.
4,989,607 A * 2/1991 Keusch et al. ............ 600/391
5,579,919 A * 12/1996 Gilman et al. ............ 206/701
5,645,571 A 7/1997 Olson et al.
5,817,151 A * 10/1998 Olson et al. .............. 607/142
5,916,244 A * 6/1999 Walters ................... 607/142
5,951,598 A 9/1999 Bishay et al.
5,984,102 A * 11/1999 Tay ....................... 206/701
6,101,413 A * 8/2000 Olson et al. ................ 607/5
6,272,385 B1 8/2001 Bishay et al.

(Continued)

FOREIGN PATENT DOCUMENTS

EP    0894509 A    2/1999

(Continued)

*Primary Examiner*—Carl H Layno
*Assistant Examiner*—Luther G Behringer
(74) *Attorney, Agent, or Firm*—W. Brinton Yorks, Jr.

(57) ABSTRACT

The present invention provides a self-storing medical electrode (10) that does not require packaging, enclosures, or other means to house and to protect various electrode components. According to one aspect, the invention provides an electrode comprising an electrode body having first and second sides, wherein the first side comprises a barrier layer (15) comprising a heat-sealable material and the second side comprises a conductive layer (16). The electrode further comprises an electrically conductive gel layer (18) disposed on the electrode body and which is further in electrical communication with the conductive layer (16).

20 Claims, 3 Drawing Sheets

U.S. PATENT DOCUMENTS

| | | | |
|---|---|---|---|
| 6,694,193 B2 | 2/2004 | Lyster et al. | |
| 6,935,889 B2 * | 8/2005 | Picardo et al. | 439/521 |
| 2004/0260376 A1 * | 12/2004 | Craige et al. | 607/142 |
| 2007/0060993 A1 * | 3/2007 | Craige et al. | 607/142 |

FOREIGN PATENT DOCUMENTS

| | | | |
|---|---|---|---|
| EP | 1195137 A | | 4/2002 |
| WO | WO 2005/092340 | * | 10/2005 |

* cited by examiner

SELF-STORING MEDICAL ELECTRODES

CROSS REFERENCE TO RELATED APPLICATION

This application claims the benefit of U.S. provisional application Ser. No. 60/556,132 filed Mar. 23, 2004, which is incorporated herein.

The present invention relates in general to electrodes for medical instruments, and more particularly, to self-storing medical electrodes in a defibrillator/pacing device and methods of making and using same.

BACKGROUND OF THE INVENTION

Sudden cardiac death is the leading cause of death in the United States. Most sudden cardiac death is caused by ventricular fibrillation ("VF"), in which the muscle fibers of the heart contract without coordination, thereby interrupting normal blood flow to the body. The only known treatment for VF is electrical defibrillation, in which an electrical pulse is applied to a patient's heart. The electrical shock clears the heart of the abnormal electrical activity (in a process called "defibrillation") by depolarizing a critical mass of myocardial cells to allow spontaneous organized myocardial depolarization to resume.

One way of providing electrical defibrillation is by automatic or semi-automatic external defibrillators, collectively referred to as "AEDs," which send electrical pulses to a patient's heart through electrodes applied to the torso to defibrillate the patient or to provide for external pacing of the patient's heart. The use of AEDs by untrained or minimally trained operators for a patient in sudden cardiac arrest is a time critical operation. The electrical pulse must be delivered within a short time after onset of VF in order for the patient to have any reasonable chance of survival.

Thus, simplifying and minimizing the number of steps required by the operator to defibrillate and improving the reliability of defibrillation increases key aspects of an AED design. The AED is typically stored with electrodes that are sealed in an enclosure that protects the electrodes from contamination and retards desiccation. Before defibrillation can commence the operator must open the enclosure, remove the electrodes, and apply them to the patient. Electrodes that are sealed with a connector inside an enclosure, such as a bag, can require multiple steps by the operator. First, the operator must open the sealed bag. Second, the operator must plug the electrodes into the AED. Third, the operator must remove a release liner, which typically covers a gel on the electrode pads from the first electrode and fourth, the operator must place the electrode on the patient. The operator must then repeat the fourth step with the second electrode and place the second electrode on the patient.

The electrodes typically comprise a non-conductive base layer such as a plastic disc and a conductive layer that distributes the current transmitted to the electrode by the defibrillator. The base layer is typically constructed of a thin, flexible polymeric material such as urethane foam, or a polyester or polyolefin laminate which is electrically insulating and provides structural integrity to the electrode. Conventionally, such electrodes further include a layer of adhesive material that is used to adhere the electrode to the patient's chest prior to and during delivery of the shocks. The adhesive material is typically a viscous water-based gel material that contains ionic compounds which increase the material's electrical conductivity to provide a low resistance path for current to flow from the electrode to the patient's chest.

As is known in the art, electrodes used with automatic external defibrillators often are stored for relatively long periods of time until needed. During this time, the adhesive material can become desiccated. This desiccation decreases the effectiveness of the material in that it lowers the material's conductivity, which in turn raises the impedance at the contact area between the electrode and the skin. This increased impedance results in less current reaching the heart. Due to the problem of desiccation, the adhesive material normally is covered with a removable backing that reduces the material's exposure to air. Despite the provision of such backings, however, conventional adhesive materials still tend to dry out. For the purpose of preventing such desiccation, modern medical electrode packaging typically provides a sealed electrode storage environment and through-wall electrical connectivity to electrotherapy devices such as external defibrillators. The electrode packaging is typically either a flexible, heat-sealable laminate material, or a rigid, molded plastic material, both of which serve as a moisture barrier.

Flexible electrode housings such as foil-lined plastic bags provide economical and simple packaging for electrodes in many instances. Electrode wires may extend through the exteriors of known flexible housings, and connect directly to electrotherapy devices. A seal around the wires is typically achieved by heat-sealing the packaging material to the wires or by molding a plastic piece around the wires and sealing the packaging material to the piece. The electrodes themselves are typically arranged in the package so that they form an electrical circuit between themselves and the associated medical device. Prior art flexible housings, however, suffer from several drawbacks. Electrode function or sterility, for instance, may be compromised when electrode wiresets protrude through the flexible housing. For example, flexing may weaken the bond between the electrode wireset and the flexible material. In addition, the flexible material of the packaging may remain adhered to the electrode wires after placement of the electrodes on a patient, causing user confusion or delay. Further, adequately sealing areas where the electrode wires extend through flexible housings continues to present challenges and may increase manufacturing costs or complexity.

Rigid structures offer an alternative to flexible housings. Walls of rigid structures may include insert-molded electrical contacts, such as pins, which provide through-wall electrical connectivity between enclosed electrode wires and external electrotherapy devices. Thus, the electrode wires do not exit the cartridge, but rather, are permanently attached to electrical contacts that pass through the wall of the rigid structure. These electrical contacts complete the electrical connection to the intended device. Although rigid housing structures may sometimes be more expensive and have higher manufacturing costs than flexible housings, rigid structures are often selected because they have been designed to enclose electrode wiresets without compromising the seals of the structure, and they offer relatively simple user interfaces. Rigid structures, however, may be less desirable in some applications, such as at high altitudes, when pressures inside the structures greatly exceed ambient pressures. Also, heat-seal film, which is often stretched over rigid structure openings, may be vulnerable to puncture.

In addition to these disadvantages, these prior art electrode packaging materials, whether rigid or flexible, are external to the electrode and must be disengaged from the electrodes prior to deployment of the electrodes. For instance, prior art packaging comprising a flexible, heat-sealable pouch or envelope-style structure must be torn and removed and any sort of release liner or backing material adhered to the conductive gel must be stripped away in two separate steps. These are steps which reduce the efficiency of the device operator during a life-saving process such as cardiac defibrillation. There is a long-standing need for an electrode storage system that is integrated within and is part of the electrode itself and that prevents desiccation of the electrically conductive gel materials contained therein. Such a self-storing electrode would allow for long-term sealed storage of the electrodes and ease of operation of the electrodes without the limitations of prior art flexible and rigid housings, particularly flexible housings that must be torn off prior to use. In addition, such self-storing electrode would be useful in a wide array of applications for both receiving and transmitting current such as, for example, in cardiac defibrillation.

SUMMARY OF THE INVENTION

The present invention meets the aforementioned needs by providing a self-storing medical electrode that does not require packaging, enclosures, or other means to house and to protect the electrode during long-term storage.

According to one embodiment, the invention provides an electrode comprising an electrode body having first and second sides, wherein the first side comprises a flexible barrier layer comprising a heat-sealable material and the second side comprises a conductive layer. The electrode further comprises an electrically conductive gel layer disposed on the electrode body and which is further in electrical communication with the conductive layer.

According to another embodiment, the invention provides an electrode system comprising a pair of electrodes disposed on opposite sides of a non-conductive release liner, wherein the electrodes are in electrical contact with each other through a conductive element that is disposed within the non-conductive release liner and which is in electrical contact with both electrodes. An electrically conductive gel layer is interposed between the conductive layer and the non-conductive release liner, and the gel layer is in electrical contact with the conductive element disposed within the non-conductive release liner.

In yet another embodiment, the invention provides a method of manufacturing a self-storing electrode system comprising providing two electrode bodies each having a first and second side, wherein the first side comprises a flexible barrier layer comprising a heat-sealable material and the second side comprises a conductive layer.

According to one embodiment of this invention, the electrode body is placed on opposite sides of a non-conductive release liner, and each side has a recessed portion containing an electrically conductive gel, and the non-conductive release liner contains a conductive element which is electrically connected with the electrically conductive gel on either side of the non-conductive release liner. A lead wire is affixed to each electrode by a connecting means that electrically connects the lead wire to the conductive layer of each electrode. Preferably heat or other sealing means as discussed below is applied to the flexible barrier layers to form a heat seal or other moisture-proof seal between the flexible barrier layer and the non-conductive release liner.

DETAILED DESCRIPTION

Figure 1:
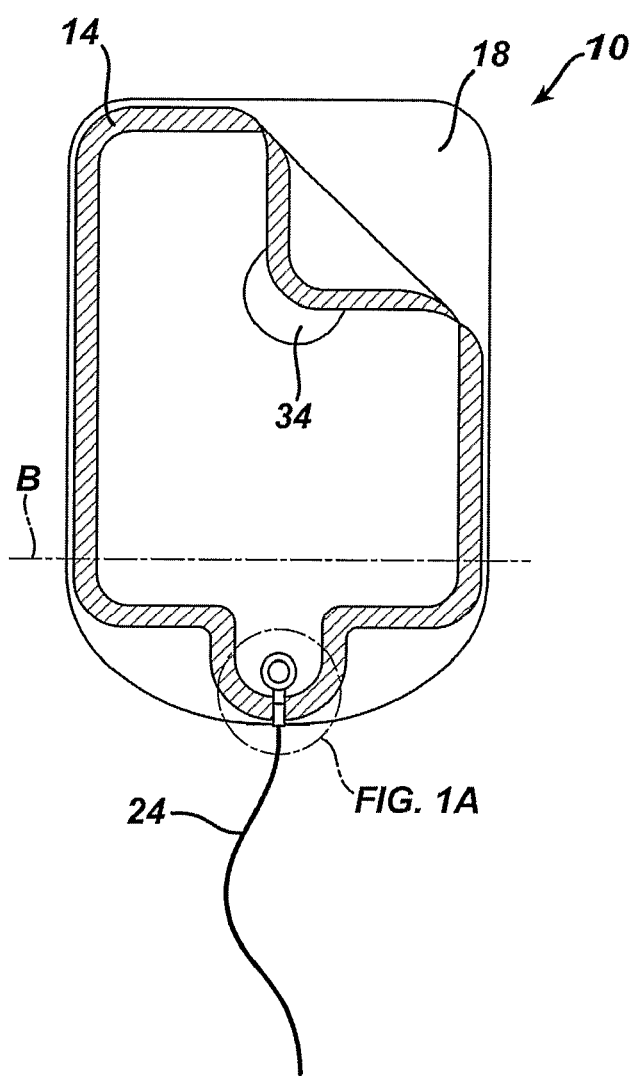
FIG. 1 provides a top view of a electrode assembly usable in connection with embodiments of the present invention that is disposed on a non-conductive release liner, with a portion of the electrode peeled back to reveal the various layers of the electrode. Detail A provides a detailed cross-sectional side view of the detailed portion A of the electrode.
Figure 1A:
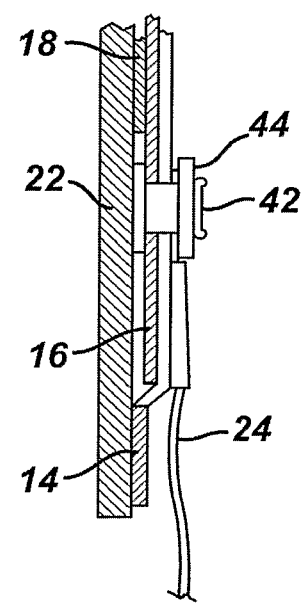

Turning now to the drawings, wherein like numerals designate like components, FIG. 1 illustrates a top view of a medical electrode assembly 10 usable in connection with aspects of the present invention comprising an electrode 12 that is disposed on a non-conductive release liner 22, with a portion of the electrode 12 peeled back via a peel tab 34 to reveal the various layers of the electrode assembly 10. The elements of a medical electrode 12 according to this embodiment of the present invention comprise an electrode body having a first and a second side, wherein the first side comprises a flexible barrier layer 14 comprising a heat-sealable material 15 and the second side comprises a conductive layer 16. The medical electrode 12 further comprises an electrically conductive gel layer 18 disposed on the electrode body 12 and which is in electrical communication with the conductive layer 16. The gel layer 18 is adjacent to non-conductive release liner 22.

As shown in Detail A of FIG. 1, the flexible barrier layer 14 comprising the heat sealable layer 15 overlies and is coupled to the conductive layer 16, which in turn is disposed over the gel layer 18. The gel layer 18 is placed adjacent to the non-conductive release liner 22. In some embodiments, the electrode further comprises a lead wire 24 that electrically connects the electrode to a medical device (not shown) such as an AED. As shown in Detail A, in one embodiment the electrode comprises a lead wire 24 that is connected to the flexible barrier layer 14 of the electrode 12 and which electrically connects the electrode 12 to a medical device. As would be appreciated by one of skill in the art, the lead wire 24 can be electrically connected to the electrode 12 by a connector 28 or connecting means, including but not limited to, a rivet, ring tung terminal, staple, grommet, screw, bolt, or a pin connector or other electrically conducting fastening means which is capable of causing electrical signals, or representations thereof, to traverse the flexible barrier layer 14 to the conductive layer 16. Thus, connector 28 can be disposed such that the lead wire 24 passes around, and not through, the heat seal seam formed by flexible barrier layer 14 and non-conductive release liner 22.

In certain embodiments the connector 28 is applied using standard grommet or rivet means and materials. For example, as shown in Detail A of FIG. 1, a rivet 42 which traverses the flexible barrier layer 14 and the conductive layer 16 of the electrode 12 is held in place by a washer 44. This connector 28 presses against the flexible barrier layer 14, resulting in a tight, form-fitting seal between the connector 28 components and the flexible barrier layer 14, similar to plumber's tape (polytetrafluoroethylene) that is used to seal pipe fittings together.

As will be appreciated by one of skill in the art, the conductive layer 16 may comprise any of a number of prior art means for transferring current or voltage to the gel layer 18.

Specific examples include thin layer strips of a conductive material such as a metal sheet or foil, or a laminate composition comprising a metal such as tin foil and a polymeric or other substrate material to provide physical support such as polyester.

In some other embodiments, the conductive layer 16 comprises a conductive ink that is printable on a substrate surface. For example, the conductive layer 16 may comprise a silver and carbon/graphite-based ink and any number of resins that are applied to the surface of a printable surface such as polyvinylchloride, polypropylene or another polymer substrate.

Figure 2:
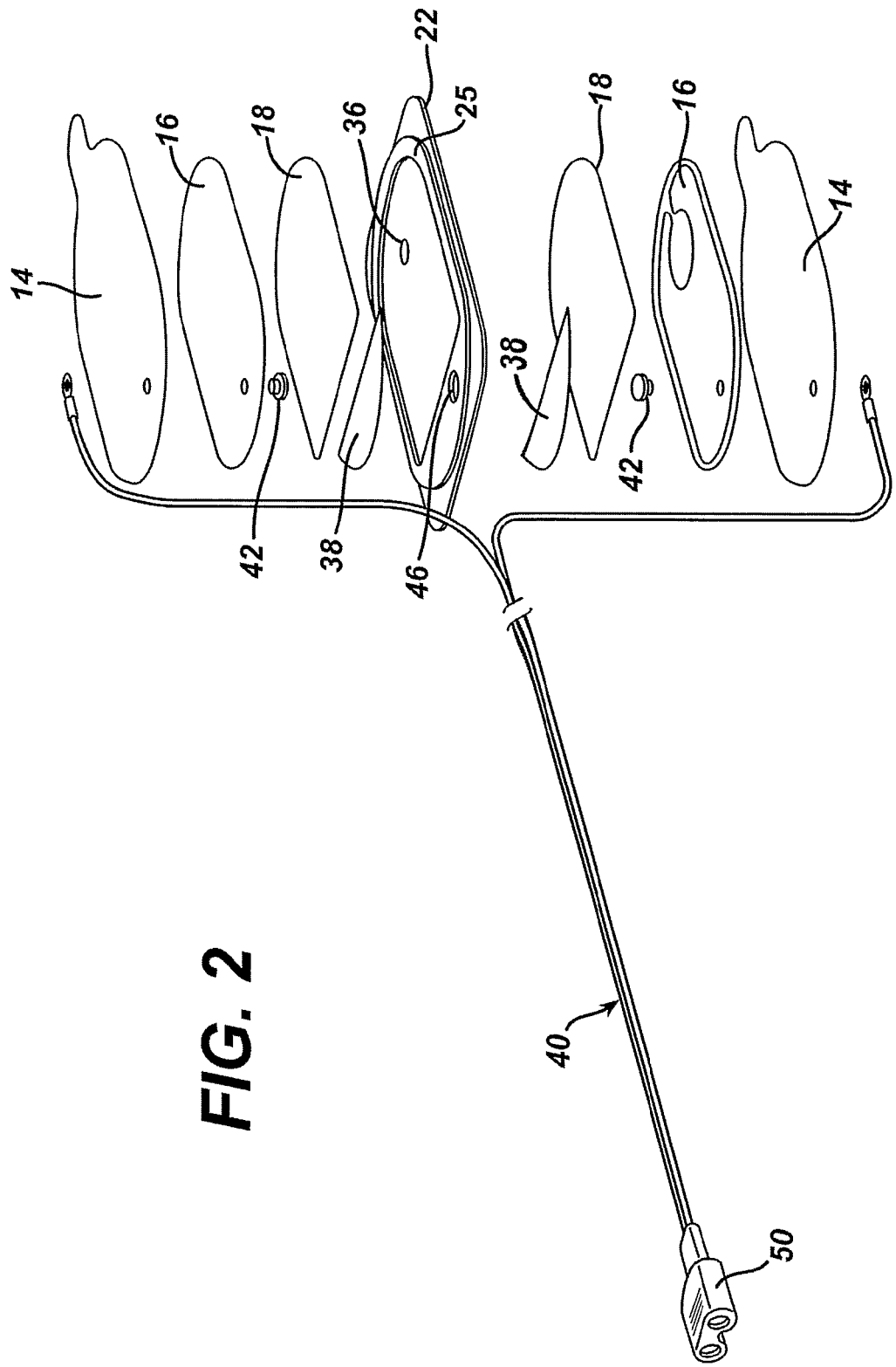
FIG. 2 provides an exploded perspective view of an electrode system in accordance with another embodiment of the present invention comprising a pair of electrodes disposed on opposite sides of a backing and illustrating connections for connecting the system to an external medical device.

In yet another embodiment, and as illustrated by an exploded perspective view in FIG. 2, the present invention provides an electrode system 10 comprising a pair of electrodes 12 disposed on opposite sides of a non-conductive release liner 22, wherein the electrodes 12 are in electrical contact with each other through a conductive element 36 that is disposed within the non-conductive release liner 22 and which is in electrical contact with both electrodes 12 via the electrically conductive gel layer 18. The use of a common non-conductive release liner 22 for both electrodes provides a convenient means of maintaining electrical contact between them, whether by the conductive element 36 as shown in FIG. 2 or any other means known in the prior art, including a single conductive strip extending from the conductive layer 16 of one electrode 12 to another, or separate conductive strips extending from the conductive layer and meeting at the periphery of the non-conductive release liner 22, such that electrical communication between the electrodes 12 is maintained.

Electrodes for transmitting electrical energy such as those used in a pacer/defibrillator obtain energy from an electrical source 40. An electrical circuit is completed through the circular loop at the proximal ends of the lead wires 24 which are in electrical communication with a connector 28 such as a conductive rivet 42 which impregnates, traverses, penetrates, or otherwise extends through both the flexible barrier layer 14 and the conductive layer 16. The distal end of the lead wire 24 connects with a cable 48 that connects with a connector plug 50 or other means for plugging to an external medical device such as an AED. Since it is desirable that any electrical charge carried from a defibrillator or other medical device to the patient through the lead wire occurs in a controlled manner during defibrillation and not while the operator is carrying out preparatory steps prior to deployment, in some embodiments an insulating layer 38 is provided. Removal of the electrode 12 from the backing 24 exposes the rivet 42. In order to protect the operator from physical contact with the connector 28 which is electrically connected to an electrical source 40, the electrode further comprises an insulation layer 38 interposed between a portion of the conductive layer 16 and the non-conductive release liner 22 such as the heel-shaped insulating layer 38 shown in FIG. 2.

In the embodiment shown in FIG. 2, the non-conductive release liner 22 has two sides, each side having a recessed portion 25. The recessed portion 25 is shaped to store the electrically conductive gel layer 18 of each electrode. In other embodiments, the non-conductive release liner 22 includes a second recessed portion 46 that accommodates the contours of the connector 28 such as the rivet 42 such that a generally flat and thin geometry of the electrode assembly is achieved.

In some embodiments, the heat-sealable material 15 comprises a thermoplastic polymeric material. As used herein, a "heat sealable" or "heat seal coated" material refers to a substrate that readily forms a seal between itself and another surface of a like or different substrate with the application of heat. Some heat sealable or heat seal coated materials are also effective as vapor, moisture or air barriers. Typically, the heat-sealable material comprises a thermoplastic polymeric material. A variety of heat sealable and heat seal coated materials are commercially available, and are within the scope of the present invention. For example, in some embodiments the heat sealable material comprises films of polyethylene, spun-bonded polyolefin (TYVEK®, DuPont, Wilmington, Del.), polyvinyl chloride, ionomer resin, polyamides, polyester, polypropylene, polycarbonate, or polystyrene. A heat-sealable flexible laminate material suitable for use with the present invention is commercially available from Cadillac Products, Inc. in Troy, Mich.

As would be appreciated by one of skill in the art, the heat-sealable flexible material could alternatively be comprised of two layers, including a moisture barrier layer 17 under a separate heat-sealing layer 15. The layers may also be arranged in a different order. Thus, in one embodiment, the flexible barrier layer 14 further comprises a vapor or oxygen/air barrier material 17 comprising a polymeric film or sheet, a foil material, or a coated substrate comprising a metal, textile, paper, or non-woven material coated with a polymeric material. Some exemplary vapor or air barrier materials 17 preferably comprise a laminate such as a metallized polyester that has been laminated to low-density polyethylene (MPPE). In another embodiment, the vapor or air barrier comprises a fluoropolymer film such as polychlorotrifluoroethylene (e.g., ACLAR®, Honeywell).

Figure 3:
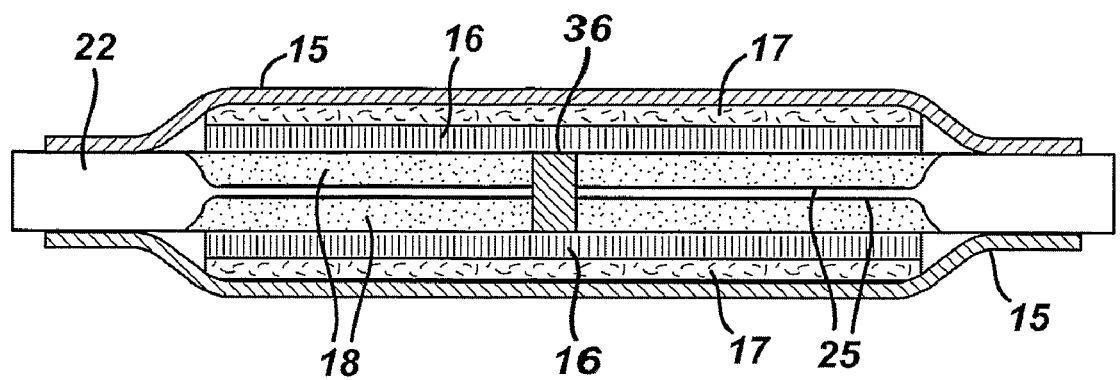
FIG. 3 provides a cross-sectional view of the electrode assembly of FIG. 1 along line B.

Referring now to FIG. 3, a cross-sectional view of the electrode assembly 10 of FIG. 1 along line B illustrates another embodiment. The flexible barrier layer 14 comprises a laminate comprising a first layer of a heat-sealable outer layer 15 disposed over a second layer of a vapor or air barrier 17. For example, the flexible barrier layer 14 comprises a polyolefin heat sealable layer 15 such as polyethylene disposed over a second layer of a vapor barrier 17 comprising a fluoropolymer film such as polychlorotrifluoroethylene, commercially available as ACLAM®, from Honeywell or a polymer laminate such as MPPE. A conductive element 36 traverses the thickness of the non-conductive release liner 22, such that it is in electrical communication with the conductive layer 16 of the electrodes on either side of the non-conductive release liner 22 (and therefore, the electrodes are in electrical communication with each other).

The gel layer 18 may comprise any number of widely-available conductive compounds that maintain direct electrical contact with the skin and permits continued contoured adhesion to the body of a patient. The gel layer 18 may preferably also possess a pressure sensitive quality to promote adhesion to the body of a patient.

As will be appreciated by one skilled in the art, a wide variety of substrates may be utilized as a non-conductive release liner 22 in the practice of the present invention. Typically, such non-conductive release liner 22 material is chosen such that the electrically conductive gel layer 18 of the electrode 12 will readily peel away from the non-conductive release liner 22 while remaining attached to the electrode body 12. In some preferred embodiments, the non-conductive release liner 22 comprises a polymeric sheet such as high-density polyethylene, a coated paperboard, or foam, such that the backing provides a relatively rigid surface with respect to the flexible electrode 12 which is peeled away from the backing just prior to use.

To facilitate ease of removal of the heat sealed electrode 12 from each side of the backing material 22, in some embodiments the non-conductive release liner 22 comprises a material treated with an adhesion-reducing agent such as a surface-treated polymeric sheet. For example, the non-conductive release liner 22 may comprise siliconized polyethylene, polypropylene, polyester, acrylate, polycarbonate, or wax or plastic coated paperboard or foam. An adhesion-reducing agent as used herein refers to an agent that, when applied to a substrate, reduces the coefficient of friction of that substrate. In other embodiments, depending on the choice of heat-sealable material 14 that is chosen, the release liner 22 may comprise an uncoated or non-surface treated substrate from which the heat-sealable material 14 will readily peel off. In other embodiments, at least a portion of the recessed portion 25 of the release liner 22 that comes into contact with the electrically conductive gel layer of the electrode is coated with an adhesion-reducing material such that the gel separates cleanly from the backing. Other portions of the release liner 22 that are sealed directly to the heat-sealable layer 15 are left uncoated since it is desired that a strong heat seal be maintained between the release liner and the heat-sealable layer 15 during extended storage of the electrodes 12.

The present invention also provides a method of manufacturing a self-storing electrode system comprising providing two electrode bodies 12 each having a first and second side, wherein the first side comprises the flexible barrier layer 14 comprising a heat-sealable material 15 and the second side comprises the conductive layer 16. According to one embodiment of this aspect, the electrode body 12 is placed on opposite sides of the non-conductive release liner 22, and each side has a recessed portion 25 containing the electrically conductive gel 18, and the non-conductive release liner 22 contains a conductive element 36 which is electrically connected with the electrically conductive gel 18 on either side of the non-conductive release liner.

Preferably heat or other sealing means such as pressure is applied to the flexible barrier layer 14 to form a vapor, air and/or moisture-proof seal between the flexible barrier layer 14 and the non-conductive release liner 22. As discussed above, the flexible barrier layer 14 in some embodiments may comprise a vapor or air barrier material 17 comprising a polymeric film or sheet such as a fluoropolymer film, a foil material, or a coated substrate comprising a metal, textile, paper, or non-woven material coated with a polymeric material. The flexible barrier layer may also comprise a laminate comprising a first layer of a heat-sealable material such as polyethylene disposed over a second layer of a vapor barrier such as a fluoropolymer film.

Figure 4:
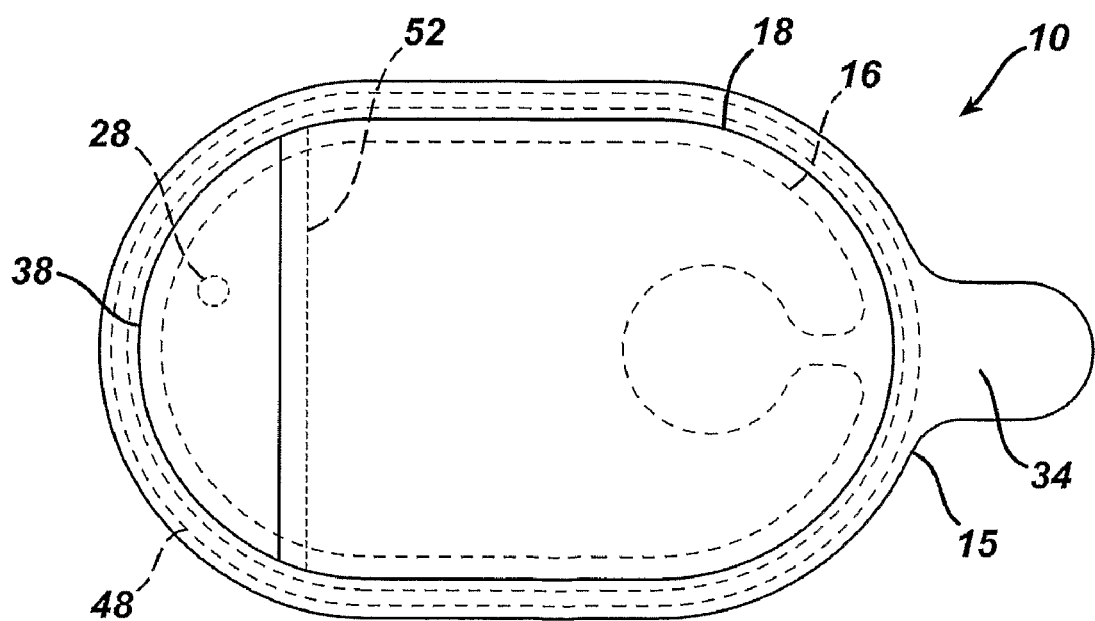
FIG. 4 provides a top semi-transparent view of a partially assembled electrode assembly in accordance with an embodiment of the present invention.

FIG. 4 is a semi-transparent top view of a partially fabricated electrode assembly 10 of the present invention, illustrating the relative geometry and placement of the heat-sealable layer 15, the conductive layer 16, and the electrically conductive gel 18 with respect to one another. It is desirable that the heat sealable layer 15 be disposed over the entire surface of the underlying electrically conductive gel 18 and the conductive layer 16 and even more desirably, extend over the periphery of the underlying layers such that a heat seal zone 48, for example, the area of the heat-sealable layer 15 between the dotted lines indicated in FIG. 4, may be formed near the periphery of the heat seal layer 15.

In this embodiment a semi-circular insulating layer 38 covers a portion of the electrode containing an electrically conductive connector 28 such as a rivet 42. One edge 52 of the insulating layer 38 is partially disposed under the electrically conductive layer 18 such that the rivet 42 is electrically isolated from the electrically conductive layer 18 and remains covered during deployment of the electrode on the patient. A seal is created in the heat-sealing zone 48 around the perimeter of the heat-sealable layer 15 by applying heat or in other ways such as application of hot-melt adhesive or double-sided adhesive tape or ultrasonic welding, for example.

The electrode assembly 10 of the present invention may be used with an electrotherapy system such as an automatic or manual external defibrillator system, or another type of electrotherapy system such as pacing or cardiac monitoring systems. A defibrillator system typically includes an energy source which provides voltage or current pulses. A controller operates an energy delivery system to selectively connect and disconnect energy source to and from one or more electrodes electrically attachable to a patient. A defibrillator system may further include elements such as user input and/or output devices or displays, memories, or computer-executable instructions implemented in software, firmware, hardware or a combination thereof.

Communication between a medical device and the electrode assembly 10 may be established via a connector plug 50 when a portion of the medical device, such as a connection for energy delivery from an energy source is coupled to one or more lead wires 24 via a cable 48. Thus, when the electrodes 12 are assembled in accordance with aspects of the present invention and when the medical device is coupled to lead wires 24 via a cable 48, the electrodes 12 remains responsive to the medical device during shipping, storage or use.

For example, communication may be established between an electrode assembly 10 and a medical device for purposes of testing the functionality of the electrode 12 while the medical device is in standby mode, and the medical device and/or electrodes 12 may be enabled to alarm if a problem is detected.

In another example, communication between the electrodes 12 and the medical device may be used to monitor other parameters of interest, such as the interior environmental conditions of the electrodes 12. Additional connections such as signal conductors could be used to facilitate monitoring of such additional parameters.

In a further example, there may be continual communication between the medical device and the electrodes 12 during normal operation of the medical device in connection with patient therapy. In the case of a defibrillator, for example, an electrode 12 may be placed on a patient and the defibrillator may continue to provide/receive electrical communication and information to/from electrode 12 via medical device during patient treatment and monitoring, without further user intervention.

The electrode assembly 10 of the present invention provides flexible manufacturing/assembly and a streamlined procedure for readying the electrodes for deployment on a patient that reduces set-up time. Integrating heat-sealable flexible materials and vapor and air barrier materials directly into the electrode itself and sealing the electrode directly to a backing material provides superior electrode storability and longevity. Such self-storing electrodes 12 remain responsive to electrotherapy devices and may be monitored for functionality and used for patient therapy without interruption of the connection from the electrotherapy device.

What is claimed is:

1. An electrode system comprising:
 a pair of electrodes disposed on opposite sides of a rigid non-conductive release liner from which the electrodes may be peeled and removed, wherein each electrode comprises an electrode body having first and second sides, wherein the first side comprises a flexible, non-conductive moisture barrier layer having a sealable periphery and the second side comprises a conductive layer, and an electrically conductive gel layer interposed between the conductive layer and the rigid non-conductive release liner in a vapor, air, and/or moisture-proof enclosure formed by the sealing of the periphery of the moisture barrier layer of each electrode to the release liner to enclose the gel layer of each electrode in a moisture barrier enclosure on its respective side of the rigid release liner.

2. The electrode system of claim 1, wherein each electrode further comprises a lead wire that is connected through said first side to said second side of the electrode and which electrically connects the electrode to a medical device.

3. The electrode system of claim 2, wherein the lead wire is electrically connected to the conductive layer and the electrically conductive gel by a connector comprising a rivet, ring tung terminal, staple, grommet, screw, bolt, or other electrically conducting fastening means that extends from the flexible non-conductive release liner through the conductive layer.

4. The electrode system of claim 3, wherein the electrode further comprises an insulation layer interposed between a portion of the conductive layer and the non-conductive release liner, wherein the insulation layer protects an operator of the electrode from physical contact with the connector which is electrically connected to an electrical source.

5. The electrode system of claim 1, wherein the non-conductive release liner comprises a polymeric sheet, coated paperboard, or foam.

6. The electrode system of claim 1, wherein the non-conductive release liner comprises a material treated with an adhesion-reducing agent comprising a surface-treated polymeric sheet comprising siliconized polyethylene, polypropylene, polyester, acrylate, polycarbonate, or wax or plastic coated paperboard or foam.

7. The electrode system of claim 1, wherein the conductive layer comprises a laminate comprising tin foil and polyester.

8. An electrode system comprising:
a pair of electrodes disposed on opposite sides of a rigid non-conductive release liner from which the electrodes may be peeled and removed, wherein each electrode comprises an electrode body having first and second sides, wherein the first side comprises a flexible, non-conductive moisture barrier layer having a sealable periphery and the second side comprises a conductive layer, and an electrically conductive gel layer interposed between the conductive layer and the rigid non-conductive release liner in a vapor, air, and/or moisture-proof enclosure formed by the sealing of the periphery of the moisture barrier layer of each electrode to the release liner to enclose the gel layer of each electrode in a moisture barrier enclosure on its respective side of the rigid release liner,
wherein the electrodes are further in electrical contact with each other through a conductive path that is disposed within the non-conductive release liner and which is in electrical contact with both electrodes through said gel layers.

9. An electrode comprising:
an electrode body having a first and second side, wherein the first side comprises a flexible moisture barrier layer comprising a heat-sealable periphery with a peel tab extending therefrom and the second side comprises a conductive layer;
an electrically conductive gel layer disposed on the electrode body and which is further in electrical communication with the conductive layer, the periphery of the heat-sealable moisture barrier layer extending beyond the periphery of the gel layer; and
a rigid non-conductive release liner to which the flexible moisture barrier layer is heat-sealed around the periphery of said gel layer by a heat seal with the gel layer in contact with the release liner to form a vapor, air, and/or moisture-proof enclosure of the gel layer so that the electrode may be stored in a desiccation-retarding condition without the need for storing the electrode in a separate desiccation-retarding pouch or envelope.

10. The electrode of claim 9, wherein the heat-sealable material comprises a thermoplastic polymeric material.

11. The electrode of claim 9, wherein the flexible barrier layer further comprises a vapor or air barrier material comprising a polymeric film or sheet, a foil material, or a coated substrate comprising a metal, textile, paper, or non-woven material coated with a polymeric material.

12. The electrode of claim 9, wherein the flexible barrier layer further comprises a vapor or air barrier material comprising a fluoropolymer film.

13. The electrode of claim 9, wherein the flexible barrier layer comprises a laminate comprising a first layer of a heat-sealable layer comprising polyethylene disposed over a second layer of a vapor barrier comprising a fluoropolymer film.

14. The electrode of claim 9, wherein the conductive layer comprises a metal sheet or foil, a conductive ink, or a laminate comprising a metal component disposed over a polymeric substrate.

15. The electrode of claim 9, wherein the electrode further comprises a lead wire that is connected to the flexible barrier layer of the electrode and which electrically connects the electrode to a medical device.

16. A self-storing electrode system comprising:
first and second electrode bodies each having a first and second side, wherein the first side comprises a flexible non-conductive moisture barrier layer having a heat-sealable periphery with a peel tab extending therefrom and the second side comprises a conductive layer which does not extend to the periphery of the moisture barrier layer;
an electrically conductive gel disposed on each of the electrode bodies which is in electrical communication with the conductive layer of each electrode;
a rigid release liner sealed by a heat seal to the periphery of the flexible moisture barrier layer of each electrode body with the gel in contact with the release liner to enclose, protect and prevent desiccation of the gel layer of each electrode body without the need for a separate enclosure such as a pouch or envelope; and
a lead wire electrically coupled to each electrode body by means of a path that does not disrupt the moisture integrity of the release liner seal.

17. The self-storing electrode system of claim 16, wherein the release liner seal further comprises a heat-seal formed between the flexible barrier layer and the release liner.

18. The self-storing electrode system of claim 16, wherein the flexible barrier layer further comprises a vapor or air barrier material comprising a polymeric film or sheet, a foil material, or a coated substrate comprising a metal, textile, paper, or non-woven material coated with a polymeric material.

19. The self-storing electrode system of claim 16, wherein the flexible barrier layer comprises a laminate comprising a first layer of a heat-sealable material comprising polyethylene disposed over a second layer of a vapor barrier comprising a fluoropolymer film.

20. The self-storing electrode system of claim 16, wherein the lead wire is connected to the conductive layer of the electrode for electrically connecting the electrode to a medical device.

* * * * *